United States Patent [19]

Sugimoto

[11] Patent Number: 5,277,172
[45] Date of Patent: Jan. 11, 1994

[54] LIGHT SOURCE DEVICE FOR AN ENDOSCOPE

[75] Inventor: Hideo Sugimoto, Tokyo, Japan

[73] Assignee: Asahi Kogaku Kogyo K.K., Tokyo, Japan

[21] Appl. No.: 791,149

[22] Filed: Nov. 13, 1991

[30] Foreign Application Priority Data

Nov. 20, 1990 [JP] Japan .............................. 2-121738[U]

[51] Int. Cl.$^5$ ................................................ A61B 1/06
[52] U.S. Cl. ...................................... 128/6; 359/230; 359/236
[58] Field of Search ........................ 128/6, 4; 358/98; 359/230, 233, 236, 234; 354/62

[56] References Cited

U.S. PATENT DOCUMENTS

| | | | |
|---|---|---|---|
| 4,729,018 | 3/1988 | Watanabe et al. | 358/98 |
| 4,762,412 | 8/1988 | Ohkubo et al. | 359/233 X |
| 4,834,071 | 5/1989 | Hosoi et al. | 128/6 |
| 4,945,366 | 7/1990 | Hisamichi et al. | |
| 5,042,915 | 8/1991 | Akutsu et al. | 128/6 X |
| 5,087,122 | 2/1992 | Ostrander et al. | 359/234 X |

FOREIGN PATENT DOCUMENTS

| | | |
|---|---|---|
| 3641131 | 6/1988 | Fed. Rep. of Germany. |
| 0200217 | 8/1989 | Japan ...................................... 358/98 |

Primary Examiner—Richard J. Apley
Assistant Examiner—John P. Leubecker
Attorney, Agent, or Firm—Sughrue, Mion, Zinn, Macpeak & Seas

[57] ABSTRACT

A light source control device for an endoscope having a light source for emitting light to be incident on a light guide, a stop mechanism for varying the quantity of light to be incident on the light guide by interrupting an optical path of light, and a control device for controlling an opening of the stop mechanism. The stop mechanism includes a sensing device for sensing the opening of the stop mechanism and outputting a sensing signal to the control device. Further, the stop mechanism includes a shaft and a stop blade rotatably supported on the shaft and being disposed in the optical path such that the quantity of light passing thereby is varied by rotating the blade. The sensing device includes an arc-shaped plate fixed to the shaft and having a radius which varies in proportion to the change in arc angle, and a sensor having an opening for receiving the circumferential edge of the arc-shaped plate to sense the amount of light which passes through the opening.

7 Claims, 3 Drawing Sheets

LIGHT SOURCE DEVICE FOR AN ENDOSCOPE

BACKGROUND OF THE INVENTION

This application is based on and claims priority from Japanese Application No. HEI 2-121738 filed Nov. 20, 1990, the disclosure of which is incorporated herein.

The present invention relates to a light for an endoscope which emits rays of light to illuminate a body cavity.

Generally, a light source for an endoscope includes a stop mechanism for varying the quantity of light, which is emitted therefrom as it propagates toward a light guide, and a control system for controlling the aperture of the stop mechanism.

There are two types of control systems for the stop mechanism. The first is an open loop type in which the stop mechanism is driven by an actuator, and the second is a closed loop type in which either the aperture of the stop mechanism or the quantity of illuminated light is detected, and the detected signal is fed back to an actuator.

The open loop type of control system is arranged such that the actuator for driving the stop mechanism, a control circuit for controlling the actuator, and a setting means for setting the aperture of the stop mechanism are connected in series.

In the closed loop type of control system where the aperture is sensed, the actuator includes an aperture sensor, which senses motion of the actuator corresponding to the opening or closing of the aperture. The sensing signal is fed to the control circuit, which controls the actuator based on the sensing signal.

In the closed loop type control system in which the quantity of illumination light is sensed, a light-quantity sensor is disposed in the light path to sense the quantity of light passing through the stop mechanism. The control circuit computes the actual aperture of the stop using the sensing signal, and compares the computed value with a preset value. When the actual aperture is different from the preset value, the actuator is controlled so that the aperture of the stop mechanism is equal to the preset value.

In the stop control system of the open loop type, there is no feedback of the actual aperture value. Thus, it is rare that the preset aperture is exactly equal to the actual aperture. Therefore, it is very difficult to reliably gain the desired aperture.

On the other hand, the closed loop control system using the aperture sensor actuator can reliably set the aperture of the stop mechanism to the preset aperture. However, this type of the control system is relatively expensive thereby increases the cost of manufacturing the endoscope light source device. Further, only the actuator of the type having the aperture sensor attached thereto can be used for the stop controller. This fact remarkably reduces the freedom in designing the endoscope light source device.

The closed loop control system using the light-quantity sensor disposed in the light path is problematic when the light source is old and the quantity of light emitted therefrom is correspondingly reduced. Under this condition the aperture corresponding to the sensed light quantity is larger than that of a light source which is relatively new and emits a greater amount of light. The sensing signal does not include information regarding the different aperture size. When a preset value in the aperture setting means is changed from a value corresponding to a full closed state to a value corresponding to an opened state, the comparison of the actual aperture with the preset aperture is based on the amount of light emitted by a new light source. Accordingly, when the preset value in the aperture setting means reaches a certain level, the aperture of the stop mechanism is considered to be fully opened even if the preset value is not reached to a value corresponding to a full opened state. The aperture of the stop is inaccurately changed according to the presetting of the aperture.

A stepping motor for stepwise driving the stop mechanism may be used for the actuator in the open loop control system. However, a complicated control circuit is required for controlling the stepping motor resulting in an increased cost to manufacture the endoscope light source.

Further, when using a stepping motor, the count must always start from a completely open or closed aperture position thus consuming additional time to set the stop to the appropriate aperture.

SUMMARY OF THE INVENTION

The present invention has been made in view of the above circumstances and has an object to provide a light source device for an endoscope which can reliably open the stop of a stop mechanism as preset, and reduce the cost to manufacture the light source device.

To achieve the above object, there is provided a light source device for an endoscope having a light source for emitting light to be incident on a light guide, a stop mechanism for varying the quantity of light to be incident on the light guide, by interrupting an optical path of light, and control means for controlling an aperture of the stop mechanism, the improvement wherein the stop mechanism includes sensor means for sensing the aperture of the stop mechanism and outputting a sensing signal to the control means.

In the light source device for an endoscope thus arranged, since the sensor means is disposed in the stop mechanism and not in the motor, there is no need for using the specially designed motor with a sensor means. Rather, a general purpose motor may be used.

In the light source device, the stop mechanism may include a stop blade rotatably supported by a shaft for varying the quantity of light. The sensor means may include a pair of first and second fan-shaped plates fixed to the shaft, each of the fan-shaped plates being shaped so that the radius thereof gradually varies in proportion to the change in angle. The arc of the fan shaped plates is substantially equal to the angle of rotation of the stop blade. Further, the first and second fan-shaped plates may be coupled with each other so that the longer side edges of the first and second fan-shaped plates are disposed symmetrically with the center line of the sensor means. A pair of first and second sensors may be structured so as to respectively receive the circumferential edge of the first and second fan-shaped plates, and may be respectively positioned at the centers of the first and second fan-shaped plates when the center line of the sensor means is positioned at the mid point between the sensors. Further, the first and second sensors may coupled with an operational amplifier, contained in the control means, for producing a difference between the output signals of the first and second sensors.

With such a construction, the change in voltage of the output signals due to temperature around the first and second sensors is the same for each sensor since the sensors have the same characteristics. Therefore, the voltage difference between the output signals remains unchanged despite a temperature change. The temperature drift of the first and second sensors can reliably be compensated.

Thus, the control means controls the aperture of the stop in the stop mechanism by utilizing the output signal of the aperture sensor installed in the stop mechanism. Accordingly, the actual aperture can be reliably detected. Further, a simple structure of installing the sensor in the stop mechanism is employed resulting in a relatively low cost to manufacture the light source device.

Other objects, features, and advantages of the invention will be apparent from the following detailed description in connection with the accompanying drawings, in which:

DETAILED DESCRIPTION OF THE PREFERRED EMBODIMENTS

Preferred embodiments of a light source device for an endoscope according to the present invention will be described with reference to the accompanying drawings.

Figure 3:
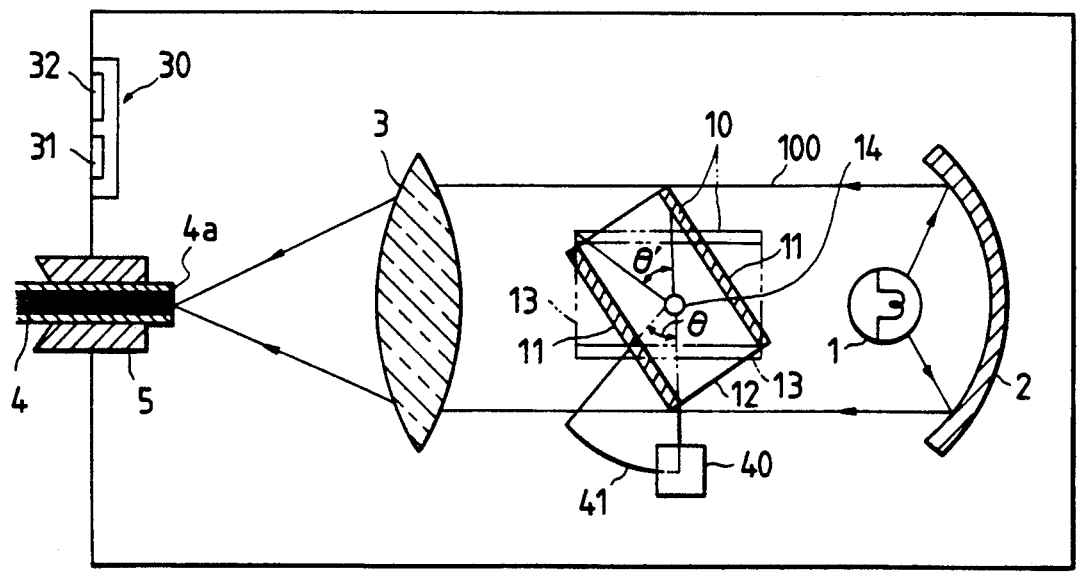
FIG. 3 is a sectional view showing the construction of the overall light source device of FIG. 1.

Referring to FIG. 3, a light source lamp 1 emits light to illuminate an object. The light rays emitted from the lamp 1 are collimated by a concave mirror 2, and are converged to the incident end face 4a of a light guide fiber handle 4 by a converging lens 3 which is disposed on the same optical axis as that of the concave mirror 2.

The incident end of the light guide fiber handle 4 is removably fastened to a connector receptacle 5 disposed on the front face of the light source device. The light rays introduced through the incident end face 4a are guided by the light guide fiber handle 4 to an illumination window (not shown) of an insertion portion of the endoscope, and are emitted outside through the illumination window.

Figure 1:
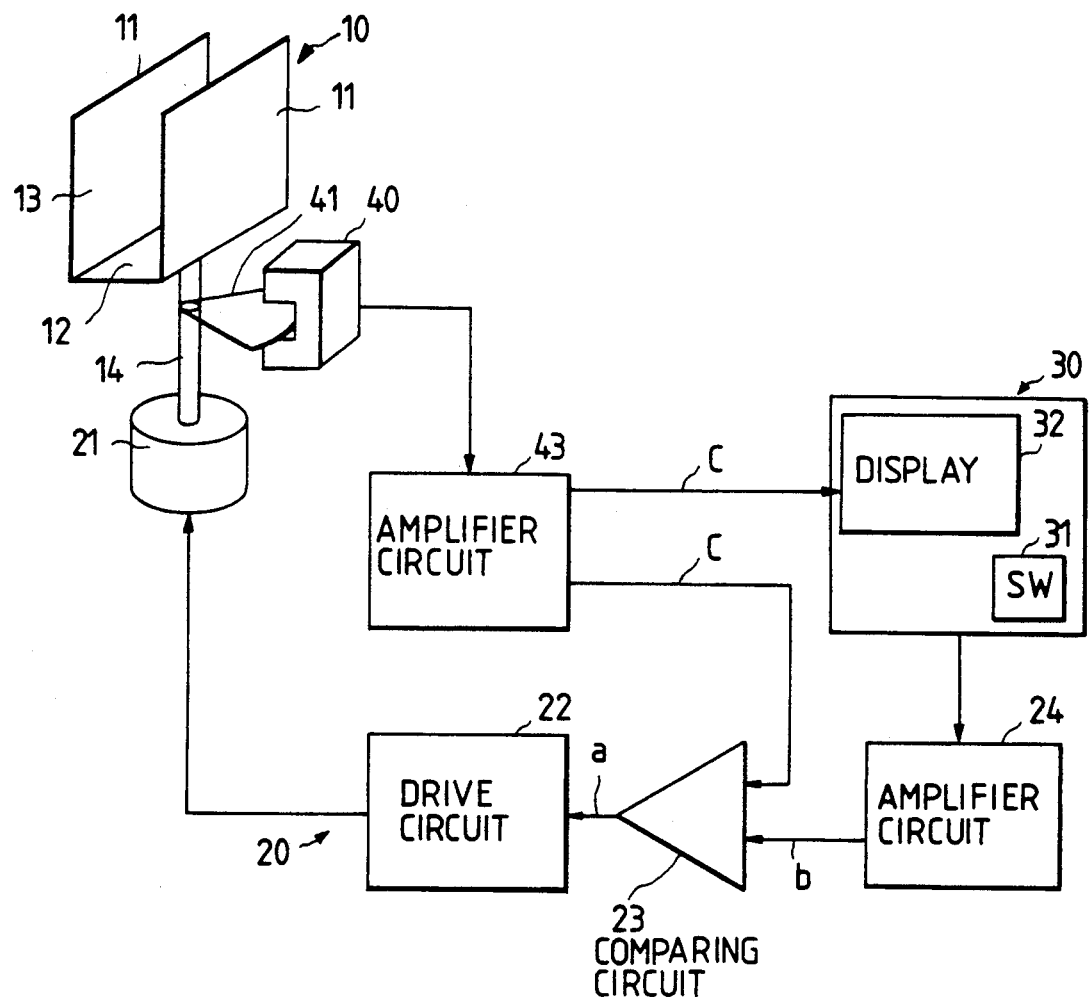
FIG. 1 is a view schematically illustrating an important portion of a light source device for an endoscope according to an embodiment of the present invention.

A stop blade 10, constituting a stop mechanism, is provided for varying the quantity of light incident on the light guide fiber handle 4. Referring also to FIG. 1, the stop blade 10 is formed with a pair of thin light shielding plates 11 and 11 arranged in parallel, and a bottom plate 12 of which the diagonal length is substantially equal to the width of an optical path 100 of light for illumination. A space defined between the shield plates 11 and 11 serves as a light passage 13 through which light passes.

As shown in FIG. 3, when the diagonal line of the stop blade 10 is substantially vertical to the optical path 100 of illumination light, the shield means 11 and 11 completely block the illuminated light. In this position, the stop blade 10 is in a completely closed state.

When the stop blade 10 is turned by angle 8 from the completely closed position such that the light passage 13 is positioned in parallel to the optical path 100, illumination light passes through the light passage 13. In this position, the stop blade 10 is in a fully opened state.

In FIG. 1, a rotating shaft 14 supports the stop blade 10 on the lower side thereof. The top end of the rotating shaft 14 is fixed to the center of the bottom plate 12 of the stop blade 10, while the bottom end is coupled with a motor 21 of control means 20. Rotation of the motor 21 is transferred to the stop blade 10, through the rotating shaft 14.

A drive circuit 22 for the motor 21 controls the rotation of the motor in accordance with a control signal "a" output from a comparing circuit 23.

An operation panel 30 is provided on the front side of the light source device. Disposed on the operation panel 30 are a switch 31 for setting an aperture of the stop blade 10, which is connected through an amplifier 24 to the input of the comparing circuit 23, and a display 32 for visually displaying the aperture of the stop blade 10.

The aperture switch 31 is able to stepwise set the desired aperture of the stop blade 10 between the fully opened state and the completely closed state. When an aperture is set by the aperture switch 31, a signal "b" representative of the set aperture is applied through the amplifier 24 to the comparing circuit 23.

A sensor means includes an aperture sensor 40 and a shield plate 41. The sensor 40 senses the actual aperture of the stop blade 10 by sensing the angle of rotation of the shield plate 41 vertically mounted to the rotating shaft 14. The sensor may be of the transmission type, such as a linear output interrupter.

Figure 2:
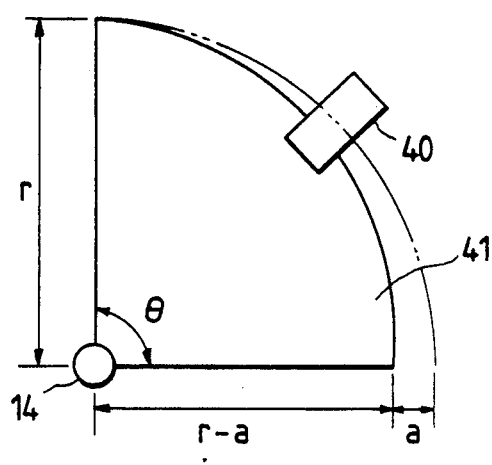
FIG. 2 is a plan view showing a shield plate used in the light source device of FIG. 1.

Referring to FIG. 2, the shield plate 41 is fan-shaped of which the center angle 8 is substantially equal to the angle $\theta'$ of rotation of the stop blade 10. The radius of the shield plate 41 gradually decreases from "r" to "r−a" varying in proportion to a change in an angle $\theta$ to a side edge having the greatest radius. Specifically, the shield plate 41 is shaped so that an area near the circumferential edge gradually decreases proportionally to the change in angle $\theta$. The shield plate 41 is fixed to the rotating shaft 14 such that the longest side edge having the radius "r" substantially coincides with the diagonal line of the bottom plate 12 of the stop blade 10, as illustrated in FIG. 3.

The aperture sensor 40 is positioned to receive the circumferential end portion of the shield plate 41 between two legs thereof. The sensor produces a voltage signal "c" which corresponds to the area of light transmitted from one leg of the sensor to the other leg across the outer circumference of the shield plate 41. Accordingly, the quantity of light transmitted from one leg to the other gradually varies with the change in angular position of the shield plate 41, so that the voltage signal "c" output from the aperture sensor 40 linearly varies with the rotation of the shield plate 41.

The output signal of the aperture sensor 40 is applied through an amplifier circuit 43 to the comparing circuit 23, and inputted through the amplifier circuit 43 to the operation panel 30. Then, it is displayed by the display 32. Since the aperture sensor 40 is not incorporated in the motor 21, there is no need to use a specially designed motor having a sensor rather, a general purpose motor may be used.

The operation of the light source device thus constructed will be described. Firstly, an operator sets the desired aperture of the stop blade 10 by operating the aperture set switch 31 on the operation panel 30. Upon the switch operation, a signal "b" representative of the set aperture is input to the drive circuit 22, through the amplifier 24 and the comparing circuit 23. The drive circuit 22 controls the rotation of the motor 21 according to the signal "b" such that the motor 21 rotates the stop blade 10 to the desired angle with respect to the optical path 100 of the illuminated light.

At this time, the shield plate 41 rotates with the rotation of the stop blade 10. The circumferential end portion of the shield plate 41 is disposed between the legs of the aperture sensor 40. The area of the circumferential end portion inserted between the legs of the sensor depends on the angular position of the stop blade 10 with respect to the optical path 100.

The aperture sensor 40 senses an angle of the stop blade 10 with respect to the optical path 100, depending on the area of light transmitted across the legs of the detector. The sensor outputs a signal "c" representing the angle, corresponding to the actual aperture of the stop blade 10, to the comparing circuit 23 through the amplifier circuit 43.

The comparing circuit 23 compares the signal "c" and the signal "b" from the aperture set switch 31. When the actual aperture represented by the signal "c" is different from the set aperture by the signal "b", the comparing circuit 23 continuously outputs a control signal "a" to the drive circuit 22, which causes the stop blade 10 to rotate so as to obtain the set aperture.

Accordingly, the drive circuit 22 continues to rotate the stop blade 10 via the motor 21 until the actual aperture represented by the signal "c" is equal to the set aperture by the signal "b". Thus, the actual aperture can be made equal to the set aperture.

The signal "c" from the aperture sensor 40 is also inputted to the operation panel 30 which in turn displays the angular position of the stop blade 10, or the aperture of the stop, on the display 32. Thus, an operator can visually recognize the angle of the stop blade 10.

Figure 4:
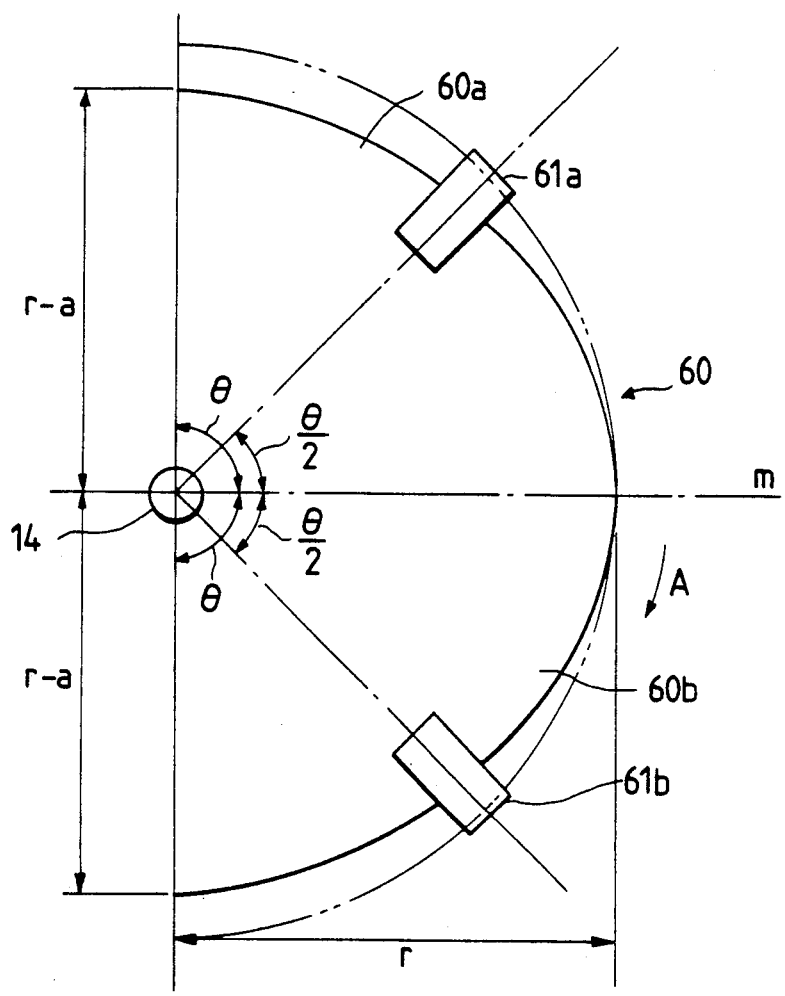
FIG. 4 is a plan view showing a shield plate used in a second embodiment of a light source device according to the present invention.
Figure 5:
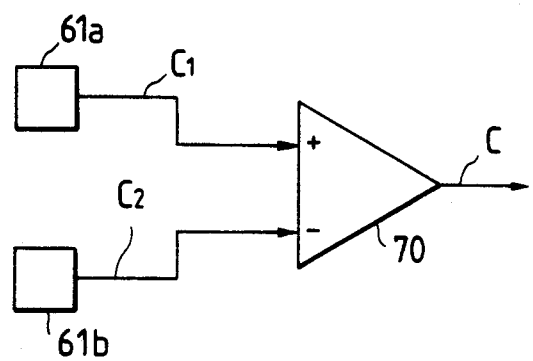
FIG. 5 is a block diagram showing an amplifier circuit used in the second embodiment.

FIGS. 4 and 5 are diagrams schematically showing a second embodiment of a light source device for an endoscope according to the present invention. FIG. 4 is a plan view showing a shield plate used in the second embodiment, and FIG. 5 is a block diagram showing an amplifier circuit.

The second embodiment is different from the first embodiment in that a shield plate 60 includes first and second shield portions 60a and 60b, each resembling the shield plate 41 shown in FIG. 1. Further, the aperture sensor means includes first and second sensors 61a and 61b each having the same characteristics as that of the aperture sensor 40.

The first and second shield portions 60a and 60b are coupled with each other so that the longer side edges of the radius "r" are symmetrically disposed with the center line "m". The first and second sensors 61a and 61b are disposed so as to be respectively positioned at the arcuate centers of the first and second shield portions 60a and 60b when the center line "m" of the shield plate 60 is positioned at the mid point between the sensors, as illustrated in FIG. 4.

In FIG. 5, an operational amplifier 70 is used in place of the amplifier circuit 43 in FIG. 1. The "+" and "−" terminals of the operational amplifier 70 are respectively connected to the output terminals of the first and second sensors 61a and 61b.

The operational amplifier 70 receives the output signals "c1" and "c2" of the first and second sensors 61a and 61b and produces a signal "c" representing a difference between the output signals "c1" and "c2".

Since the operational amplifier 70 produces a signal "c" representing a difference between the output signals "c1" and "c2", when the shield plate 60 is rotated in the direction of an arrow A, the surface area of the circumferential end portion of the first shield portion 60a decreases with respect to that of the first sensor 61a, while the surface area of the circumferential end portion of the second shield portion 60b increases with respect to that of the second sensor 61b.

With such a construction, the output signals "c1" and "c2" representing an angular position of the shield plate 41 in terms of voltage are outputted from the first and second sensors 61a and 61b, respectively. Those signals are applied to the operational amplifier 70. A difference voltage between the output signals "c1" and "c2" is output as a signal "c" from the operational amplifier 70, and applied to the comparing circuit 23.

Accordingly, if the voltages of the output signals "c1" and "c2" change due to temperature the voltages of the output signals "c1" and "c2" change by the same amount, since the sensors have the same characteristics. Therefore, the voltage difference between the output signals "c1" and "c2" remains unchanged despite the temperature change. Thus, the temperature drift of the first and second sensors can reliably be compensated. Accordingly, the operational amplifier 70 produces the signal "c" indicative of the actual aperture of the stop blade 10 for transfer to the comparing circuit 23, without any adverse effect from the temperature change.

As seen from the foregoing description, in the light source device of the invention, the control means controls the aperture of the stop in the stop mechanism by using the output signal of the aperture sensor installed in the stop mechanism. Accordingly, the actual aperture can be reliably detected. The quantity of light can be changed by changing the aperture of the stop.

In the above-mentioned embodiments, a diagonal line of the stop blade and side edge of the shield plate are disposed in parallel. On the other hand, the present invention does not restricted by this structure. The structure is only required that the shield plate 41 is always put within the sensor means while the full closed state of the stop blade is changed to the full opened state thereof in such a manner that an area of the shield plate to be put therebetween is changed. In addition, the sensor means is not restricted such a structure in the present invention, a variety type of sensor means can be employed.

Further, a simple structure of installing the sensor in the stop mechanism is employed resulting in a reduction in cost to manufacture the light source device.

Having described specific embodiments of out bearing, it is understood that various modification of the invention are possible in light of the above teachings.

What is claimed is:

1. A device for controlling light incident on a light guide of an endoscope, said device comprising:
   a light source for emitting light along an optical path so as to be incident on the light guide;
   a stop mechanism disposed in said optical path and having an adjustable aperture for varying the quantity of light to be incident on the light guide by controllably interrupting said optical path of said light, said stop mechanism including a rotatable stop blade disposed in said optical path such that the quantity of light passing thereby is varied by rotating said blade;

a sensor for sensing the size of said aperture and for providing a sensor output signal; and control means for controlling said aperture in accordance with said sensor output signal, wherein said sensor includes an arc-shaped plate having a maximum arc angle and being rotatable about a center point thereof and being synchronized with the rotation of said stop blade, the radius of said arc-shaped plate varying in proportion to a change in arc angle of said plate so as to have a side edge having the greatest radius, said maximum angle being at least as large as the angle of rotation of the stop blade, and a aperture sensor having an opening for receiving the circumferential edge of said arc-shaped plate to sense the amount of light which passes through said opening.

2. A device for controlling light incident on a light guide of an endoscope, said light comprising:

a light source for emitting light along an optical path so as to be incident on the light guide;

a stop mechanism disposed in said optical path and having an adjustable aperture for varying the quantity of light to be incident on the light guide by controllably interrupting said optical path of said light, said stop mechanism including a rotatable shaft and a stop blade supported on said shaft and being disposed in said optical path such that the quantity of light passing thereby is varied by rotating said blade;

a sensor means for sensing the size of said aperture and for providing a sensor output signal; and control means for controlling said aperture in accordance with said sensor output signal, wherein said sensor means includes:

an arc-shaped plate having an arc angle and being fixed to the shaft at a center point thereof, the radius of said arc-shaped plate varying in proportion to a change in angle to a side edge having the greatest radius, said angle being at least as large as an angle of rotation of the stop blade; and a sensor having an opening for receiving the circumferential edge of said arc-shaped plate to sense the amount of light which passes through said opening.

3. The device according to claim 2 wherein said stop blade includes a pair of plate-like shield members arranged in parallel and having a space therebetween, and a bottom plate interconnecting said shield members so as to form a U-shaped stop blade, the diagonal length of said bottom plate being substantially equal to a width of said optical path of light, the light passing through said space.

4. The device according to claim 3 wherein said stop blade and said arc-shaped plate are disposed on said shaft such that said diagonal length of said bottom plate and said side edge of said arc-shaped plate are disposed parallel to one another.

5. A device for controlling light incident on a light guide of an endoscope, said device comprising:

a light source for emitting light along an optical path so as to be incident on the light guide;

a stop mechanism disposed in said optical path and having an adjustable aperture for varying the quantity of light to be incident on the light guide by controllably interrupting said optical path of said light, said stop mechanism including a rotatable shaft and stop blade supported on said shaft and being disposed in said optical path such that the quantity of light passing thereby is varied by rotating said blade;

a sensor means for sensing the size of said aperture and for providing a sensor output signal; and control means for controlling said aperture in accordance with said sensor output signal, wherein said sensor means includes:

a pair of first and second arc-shaped plates fixed to said shaft and having an arc angle, the radius of each of the arc-shaped plates varying in proportion to a change in angle to a side edge having a greatest radius, said arc angle being substantially equal to the angle of rotation of the stop blade, said arc-shaped plates being coupled to each other; and a pair of first and second sensors having respective openings for receiving the circumferential edges of the first and second arc-shaped plates and being respectively positioned at arc centers of the first and second arc-shaped plates when a border line between first and second arc-shaped plates is positioned at a mid point between the sensors.

6. The device according to claim 5, wherein said control means includes an operational amplifier to which said first and second sensors are electrically coupled for producing a difference between the output signals of the first and second sensors indicative of a size of said aperture.

7. The device according to claim 5, wherein said side edge having the greatest radius of said first arc-shaped plate is connected to said side edge having the greatest radius of said second arc-shaped plate in such a manner that said first and second plates are line-symmetrical about a border line with each other.

* * * * *